United States Patent
Mete et al.

(10) Patent No.: US 7,329,686 B2
(45) Date of Patent: Feb. 12, 2008

(54) SUBSTITUTED THIOPHENE COMPOUNDS

(75) Inventors: Antonio Mete, Loughborough (GB); Iain Walters, Loughborough (GB)

(73) Assignee: AstraZeneca AB (SE)

( * ) Notice: Subject to any disclaimer, the term of this patent is extended or adjusted under 35 U.S.C. 154(b) by 262 days.

(21) Appl. No.: 10/521,728

(22) PCT Filed: Jul. 15, 2003

(86) PCT No.: PCT/SE03/01214

§ 371 (c)(1),
(2), (4) Date: Jan. 18, 2005

(87) PCT Pub. No.: WO2004/009579

PCT Pub. Date: Jan. 29, 2004

(65) Prior Publication Data

US 2006/0019999 A1    Jan. 26, 2006

(30) Foreign Application Priority Data

Jul. 19, 2002    (SE)    ..................... 0202280

(51) Int. Cl.
*A61K 31/38* (2006.01)
*C07D 333/02* (2006.01)

(52) U.S. Cl. ........................... 514/438; 549/29

(58) Field of Classification Search ............. 549/61, 549/62, 68, 70, 74, 75, 29; 514/445, 447, 514/440, 438
See application file for complete search history.

(56) References Cited

U.S. PATENT DOCUMENTS 6,723,745 B2 *  4/2004  Nishi et al. .................. 514/438
6,964,976 B2 * 11/2005  Nishi et al. .................. 514/376
7,166,639 B2 *  1/2007  Wan et al. .................... 514/447

FOREIGN PATENT DOCUMENTS

| EP | 0 373 836 | 6/1990 |
|---|---|---|
| WO | WO 01/62704 | 8/2001 |
| WO | WO 01/62713 | 8/2001 |

OTHER PUBLICATIONS

Foster et al, CA113:131729, 1990.*

* cited by examiner

Primary Examiner—Rebecca Anderson
Assistant Examiner—Yong Chu
(74) Attorney, Agent, or Firm—Fish & Richardson P.C.

(57) ABSTRACT

There are provided novel compounds of formula (I) wherein $R^1$, $R^2$, $R^3$, $R^{10}$, M, Q, T, U, Y, V and W are as defined in the specification and pharmaceutically acceptable salts thereof; together with processes for their preparation, compositions containing them and their use in therapy. The compounds are inhibitors of nitric oxide synthase and are thereby particularly useful in the treatment or prophylaxis of inflammatory disease and pain

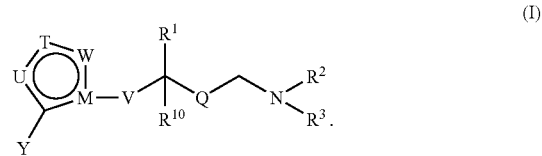

(I)

7 Claims, No Drawings

SUBSTITUTED THIOPHENE COMPOUNDS

CROSS-REFERENCE TO RELATED APPLICATIONS

This application is the national phase application under 35 U.S.C. § 371 of PCT International Application No. PCT/SE2003/001214, filed Jul. 15, 2003, which claims priority to Swedish Application Serial No. 0202280-4, filed Jul. 19, 2002.

FIELD OF THE INVENTION

The present invention relates to novel heteroarylalkylamine derivatives, processes for their preparation, compositions containing them and their use in therapy.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (eNOS) is involved with smooth muscle relaxation and the regulation of blood pressure and blood flow, whereas the neuronal enzyme (nNOS) appears to be involved in the regulation of various biological functions. Inducible NOS has been particularly implicated in the pathogenesis of inflammatory diseases. Regulation of these enzymes should therefore offer considerable potential in the treatment of a wide variety of disease states (J. E. Macdonald, *Ann. Rep. Med. Chem.*, 1996, 31, 221-230).

Considerable effort has been expended in efforts to identify compounds that act as specific inhibitors of one or more isoforms of the enzyme nitric oxide synthase. The use of such compounds in therapy has also been widely claimed.

DISCLOSURE OF THE INVENTION

According to the present invention, there is provided a compound of formula (I)

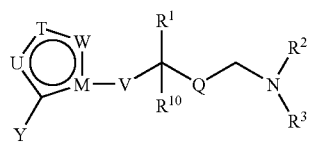

(I)

wherein:
Y represents C1 to 4 alkyl, C1 to 4 alkoxy, halogen, CN, C=CH, $NO_2$, $CH_2OH$, CHO, $COCH_3$, $NH_2$, $NHCHO$, $NHCOCH_3$, or $NHSO_2CH_3$; said alkyl or alkoxy group being optionally further substituted by one or more fluorine atoms;
T, U and W independently represent CX, N, $NR^9$, O or $S(O)_m$, except that at least one of T, U and W must represent a heteroatom and except that not more than one of T, U and W may represent $NR^9$, O or $S(O)_m$; m represents an integer 0, 1 or 2; and each X group independently represents H, C1 to 4 alkyl, C1 to 4 alkoxy, halogen, OH, SH, CN, C=CH, $N(R^{11})_2$, $NO_2$, $CH_2OH$, CHO, $COCH_3$ or NHCHO; said alkyl or alkoxy group being optionally further substituted by one or more fluorine atoms;
V represents $NR^4$, O, $CH_2$, $S(O)_n$, $OCH_2$, $CH_2O$, $NR^4CH_2$, $CH_2NR^4$, $CH_2S(O)_n$, $S(O)_nCH_2$, $CH_2CH_2$ or CH=CH;
n represents an integer 0, 1 or 2;
M represents C, and when M is bonded to a $CH_2$ moiety in V, then M may also represent N;
$R^{10}$ represents H or Me.
Q represents $(CH_2)_p$ and p represents an integer 0, 1, 2 or 3;
$R^1$ represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^5R^6$; said alkyl or alkoxy group being optionally further substituted by one or more fluorine atoms;
$R^2$ and $R^3$ independently represent H, C1 to 4 alkyl or C3 to 6 cycloalkyl; said alkyl group being optionally substituted by C1 to 4 alkoxy, halogen, hydroxy, -Z-$NR^7R^8$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;
Z represents —CO— or a bond;
and $R^4$ and $R^{11}$ independently represent H or C1 to 2 alkyl;
$R^5$, $R^6$, $R^7$ and $R^8$ independently represent H or C1 to 4 alkyl;
$R^9$ represents H, C1 to 4 alkyl, CHO, $COCH_3$, $SO_2CH_3$ or $CF_3$;
or a pharmaceutically acceptable salt thereof.

The compounds of formula (I) may exist in enantiomeric forms. It is to be understood that all enantiomers, diastereomers, racemates and mixtures thereof are included within the scope of the invention.

It will be recognised that compounds of formula (I) wherein U, T or W represents CX and X represents OH may exist in the alternative keto tautomeric form. Similarly, compounds of formula (I) wherein U, T or W represents CX and X represents NH may exist in the alternative imino tautomeric form. And similarly, compounds of formula (I) wherein U, T or W represents CX and X represents SH may exist in the alternative thioketo tautomeric form. It is to be understood that all such possible tautomeric forms and mixtures thereof are included within the scope of the invention.

The compounds of formula (I) and their pharmaceutically acceptable salts have the advantage that they are inhibitors of the enzyme nitric oxide synthase (NOS). In particular, the compounds of formula (I) and their pharmaceutically acceptable salts have the advantage that they are inhibitors of the inducible isoform of the enzyme nitric oxide synthase (iNOS).

The invention further provides a process for the preparation of compounds of formula (I) or a pharmaceutically acceptable salt, enantiomer or racemate thereof.

According to the invention there is also provided a compound of formula (I), or a pharmaceutically acceptable salt thereof, for use as a medicament.

Another aspect of the invention provides the use of a compound of formula (I) or a pharmaceutically acceptable salt thereof, in the manufacture of a medicament, for the treatment or prophylaxis of diseases or conditions in which inhibition of nitric oxide synthase activity is beneficial.

Another aspect of the invention provides the use of a compound of formula (I) or a pharmaceutically acceptable salt thereof, in the manufacture of a medicament, for the treatment or prophylaxis of diseases or conditions in which inhibition of inducible nitric oxide synthase activity is beneficial.

A more particular aspect of the invention provides the use of a compound of formula (I) or a pharmaceutically acceptable salt thereof, in the manufacture of a medicament, for the treatment or prophylaxis of inflammatory disease.

A more particular aspect of the invention provides the use of a compound of formula (I) or a pharmaceutically acceptable salt thereof, in the manufacture of a medicament, for the treatment or prophylaxis of pain.

According to the invention, there is also provided a method of treating, or reducing the risk of, diseases or conditions in which inhibition of nitric oxide synthase activity is beneficial which comprises administering to a person suffering from or at risk of, said disease or condition, a therapeutically effective amount of a compound of formula (I) or a pharmaceutically acceptable salt thereof.

More particularly, there is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt thereof.

The compounds of the present invention may also be used advantageously in combination with a second pharmaceutically active substance; particularly in combination with a cyclooxygenase inhibitor; more particularly in combination with a selective inhibitor of the inducible isoform of cyclooxygenase (COX-2). Thus, in a further aspect of the invention there is provided the use of a compound of formula (I) or a pharmaceutically acceptable salt thereof, in combination with a COX-2 inhibitor for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a compound of formula (I) or a pharmaceutically acceptable salt thereof in combination with a COX-2 inhibitor.

In one embodiment, V in formula (I) represents $S(O)_n$ and n represents 0.

In another embodiment, Y in formula (I) represents CN.

In another embodiment, $R^1$ in formula (I) represents optionally substituted phenyl or a five or six membered aromatic heterocyclic ring containing 1 to 3 heteroatoms independently selected from O, S and N. In a further embodiment, $R^1$ in formula (I) represents optionally substituted phenyl, pyridyl, thienyl, isoxazolyl, isothiazolyl or thiazolyl. In a yet further embodiment, $R^1$ in formula (I) represents optionally substituted phenyl.

In one embodiment, one of T, U and W in formula (I) represents S and the other two represent CX and M represents C.

In a particular embodiment, the compounds of formula (I) have the absolute stereochemistry as shown:

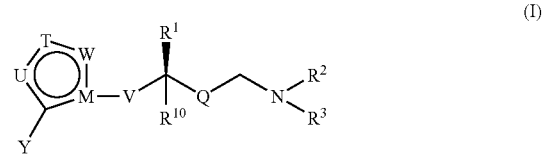

Particular compounds of the invention include:
3-[[(1S)-2-amino-1-phenylethyl]thio]-5-methyl-2-thiophenecarbonitrile;

and pharmaceutically acceptable salts thereof.

Unless otherwise indicated, the term "C1 to 4 alkyl" referred to herein denotes a straight or branched chain alkyl group having from 1 to 4 carbon atoms. Examples of such groups include methyl, ethyl, n-propyl, i-propyl, n-butyl, i-butyl and t-butyl.

Unless otherwise indicated, the term "C3 to 6 cycloalkyl" referred to herein denotes a cycloalkyl group having from 3 to 6 carbon atoms. Examples of such groups include cyclopropyl, cyclopentyl and cyclohexyl.

Unless otherwise indicated, the term "C1 to 4 alkoxy" referred to herein denotes a straight or branched chain alkoxy group having from 1 to 4 carbon atoms. Examples of such groups include methoxy, ethoxy, n-propoxy, i-propoxy and t-butoxy.

Unless otherwise indicated, the term "halogen" referred to herein denotes fluoro, chloro, bromo and iodo.

Examples of a five or six membered aromatic heterocyclic ring containing 1 to 3 heteroatoms independently selected from O, S and N include furan, thiophene, pyridine, thiazole, imidazole, oxazole, triazole, oxadiazole, thiadiazole and pyrimidine.

Examples of a five or six membered saturated heterocyclic ring containing 1 to 3 heteroatoms independently selected from O, S and N include pyrrolidine, tetrahydrofuran, piperidine and piperazine.

Examples of a "C1 to 4 alkyl or C1 to 4 alkoxy optionally further substituted by one or more fluorine atoms" include $CH_2F$, $CHF_2$, $CF_3$, $CF_3CF_2$, $CF_3CH_2$, $CH_2FCH_2$, $CH_3CF_2$, $CF_3CH_2CH_2$, $OCF_3$ and $OCH_2CF_3$.

According to the invention, we further provide a process for the preparation of compounds of formula (I), or a pharmaceutically acceptable salt, enantiomer or racemate thereof which comprises:

(a) reaction of a compound of formula (II)

wherein T, U, W, Y and M are as defined in formula (I) and $L^1$ represents a leaving group, with a compound of formula (III)

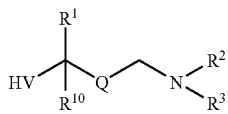
(III)

wherein $R^1$, $R^2$, $R^3$, $R^{10}$, Q and V are as defined in formula (I); or (b) reaction of a compound of formula (IV)

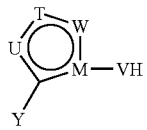
(IV)

wherein T, U, W, M, Y and V are as defined in formula (I), with a compound of formula (V)

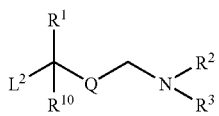
(V)

wherein $R^1$, $R^2$, $R^3$, $R^{10}$ and Q are as defined in formula (I) and $L^2$ is a leaving group; or (c) reaction of a compound of formula (VI)

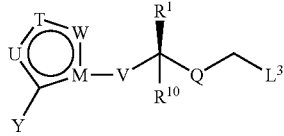
(VI)

wherein $R^1$, $R^{10}$, Q, T, U, W, M, Y and V are as defined in formula (I) and $L^3$ is a leaving group, with a compound of formula (VII)

$R^2R^3NH$ (VII)

wherein $R^2$ and $R^3$ are as defined in formula (I); or (d) reduction of a compound of formula (VIII)

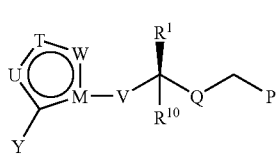
(VIII)

wherein $R^1$, $R^{10}$, Q, T, U, W, M, Y and V are as defined in formula (I) and P represents azide ($N_3$); or (e) hydrolysis of a compound of formula (VIII)

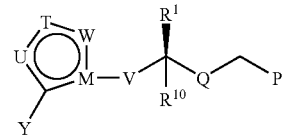
(VIII)

wherein $R^1$, $R^{10}$, Q, T, U, W, M, Y and V are as defined in formula (I) and P represents an imide group;

and where desired or necessary converting the resultant compound of formula (I), or another salt thereof, into a pharmaceutically acceptable salt thereof; or converting one compound of formula (I) into another compound of formula (I); and where desired converting the resultant compound of formula (I) into an optical isomer thereof.

In process (a), the reaction is performed by treating a nucleophile of formula (III) with an electrophile of formula (II) in an inert solvent. Suitable leaving groups $L^1$ include sulphonates and halides, particularly fluoride or chloride. The reaction is generally performed in the presence of a non-nucleophilic base such as sodium hydride or caesium carbonate. Suitable organic solvents are those such as N,N-dimethylformamide, N-methyl-2-pyrrolidinone, tetrahydrofuran, acetonitrile and dimethylsulfoxide. The reaction is generally conducted at a temperature between 0° C. and the boiling point of the solvent.

In process (b), the reactants (IV) and (V) are coupled together in a suitable inert solvent such as tetrahydrofuran using, for example, Mitsunobu conditions. Thus, for example, the reactants are treated with a phosphine derivative and an azo derivative at a suitable temperature, generally between 0° C. and the boiling point of the solvent. Suitable phosphine derivatives include triphenylphosphine and tributylphosphine. Suitable azo derivatives include diethyl azodicarboxylate, diisopropyl azodicarboxylate and 1,1'-(azodicarbonyl)dipiperidine. Suitable leaving groups $L^2$ include hydroxy.

Alternatively in process (b), the reaction is performed by treating a nucleophile of formula (IV) with an electrophile of formula (V) in an inert solvent. Suitable leaving groups $L^2$ include sulphonates and halides, particularly chloride or bromide. The reaction is generally performed in the presence of a non-nucleophilic base such as sodium hydride or caesium carbonate. Suitable organic solvents are those such as N,N-dimethylformamide, N-methyl-2-pyrrolidinone, tetrahydrofuran and dimethylsulfoxide. The reaction is generally conducted at a temperature between 0° C. and the boiling point of the solvent.

In process (c), the compounds of formulae (VI) and (VII) are reacted together in a suitable inert solvent such as dimethylsulphoxide or tetrahydrofuran. The reaction is generally carried out in the presence of a base. The base may be either an added component or an excess of the amine (VII). Suitable leaving groups $L^3$ include iodide and p-toluenesulphonate.

In processes (d) and (e), the reactions are carried out using standard conditions that will be well known to the man skilled in the art.

It will be apparent to a person skilled in the art that in the above processes it may be desirable or necessary to protect an amine or hydroxyl or other potentially reactive group. Suitable protecting groups and details of processes for adding and removing such groups may be found by reference to the standard text "Protective Groups in Organic Synthesis", 3rd Edition (1999) by Greene and Wuts.

In one preferred embodiment, amine groups are protected as carbamate derivatives, for example, as t-butyloxycarbamates.

Specific examples of the use of protecting groups are given in the Examples section.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin.

Compounds of formula (III) may be prepared by reaction of a compound of formula (IX)

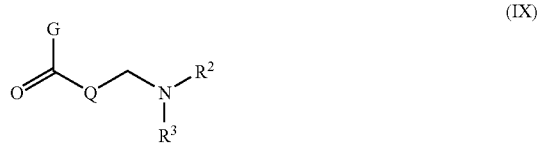

(IX)

wherein $R^2$, $R^3$ and Q are as defined in formula (I), and G represents H, Cl or $NCH_3(OCH_3)$, with an organo metallic derivative, $R^1$-M, wherein $R^1$ is as defined in formula (I) and M represents a metallic residue such as lithium or magnesium-halide, followed if necessary by reduction. The resulting compound of formula (III) wherein V represents oxygen may then be subsequently converted into compounds of formula (III) wherein V represents sulphur.

Compounds of formulae (II), (IV), (V), (VI), (VIII) and (IX) are either known or may be prepared by conventional methods that will be readily apparent to the man skilled in the art.

Intermediate compounds may be used as such or in protected form. Protecting groups and details of processes for their removal may be found by reference to the standard text "Protective Groups in Organic Synthesis", 3rd Edition (1999) by Greene and Wuts.

The compounds of the invention and intermediates thereto may be isolated from their reaction mixtures and, if necessary further purified, by using standard techniques.

The compounds of formula I may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC.

Intermediate compounds may also exist in enantiomeric forms and may be used as purified enantiomers, diastereomers, racemates or mixtures.

The compounds of formula (I), and their pharmaceutically acceptable salts, enantiomers and racemates, are useful because they possess pharmacological activity in animals. In particular, the compounds are active as inhibitors of the enzyme nitric oxide synthase. More particularly, they are inhibitors of the inducible isoform of the enzyme nitric oxide synthase and as such are predicted to be useful in therapy, for example, as anti-inflammatory agents. They may also have utility as inhibitors of the neuronal isoform of the enzyme nitric oxide synthase. In general, compounds of formula (I) and their pharmaceutically acceptable salts have the advantage that they show good selectivity for the inhibition of iNOS and/or nNOS in comparison to the inhibition of the endothelial isoform, eNOS.

The compounds and their pharmaceutically acceptable salts are indicated for use in the treatment or prophylaxis of diseases or conditions in which synthesis or oversynthesis of nitric oxide synthase forms a contributory part. In particular, the compounds are indicated for use in the treatment of inflammatory conditions in mammals including man.

Conditions that may be specifically mentioned are:
osteoartritis, rheumatoid arthritis, rheumatoid spondylitis, gouty arthritis and other arthritic conditions, inflamed joints;
eczema, psoriasis, dermatitis or other inflammatory skin conditions such as sunburn;
inflammatory eye conditions including uveitis, glaucoma and conjunctivitis;
lung disorders in which inflammation is involved, for example, asthma, bronchitis, chronic obstructive pulmonary disease, pigeon fancier's disease, farmer's lung, acute respiratory distress syndrome;
bacteraemia, endotoxaemia (septic shock), aphthous ulcers, gingivitis, pyresis, pain, meningitis and pancreatitis;
conditions of the gastrointestinal tract including inflammatory bowel disease, Crohn's disease, atrophic gastritis, gastritis varialoforme, ulcerative colitis, coeliac disease, regional ileitis, peptic ulceration, irritable bowel syndrome, reflux oesophagitis, damage to the gastrointestinal tract resulting from infections by, for example, *Helicobacter pylori*, or from treatments with non-steroidal anti-inflammatory drugs;
and other conditions associated with inflammation.

The compounds may also be useful in the treatment of cancer.

The compounds will also be useful in the treatment and alleviation of acute pain or persistent inflammatory pain or neuropathic pain or pain of a central origin.

We are particularly interested in the conditions inflammatory bowel disease, rheumatoid arthritis, osteoarthritis, chronic obstructive pulmonary disease, pain and cancer.

The compounds of formula (I) and their pharmaceutically acceptable salts may also be useful in the treatment or prophylaxis of diseases or conditions in addition to those mentioned above. For example, the compounds may be useful in the treatment of atherosclerosis, cystic fibrosis, hypotension associated with septic and/or toxic shock, in the treatment of dysfunction of the immune system, as an adjuvant to short-term immunosuppression in organ transplant therapy, in the control of onset of diabetes, in the maintenance of pancreatic function in diabetes, in the treatment of vascular complications associated with diabetes and in co-therapy with cytokines, for example TNF or interleukins.

The compounds of formula (I) may also be useful in the treatment of hypoxia, for example in cases of cardiac arrest and stroke, neurodegenerative disorders including nerve degeneration and/or nerve necrosis in disorders such as ischaemia, hypoxia, hypoglycaemia, epilepsy, and in external wounds (such as spinal cord and head injury), hyperbaric oxygen convulsions and toxicity, dementia, for example pre-senile dementia, Alzheimer's disease and AIDS-related dementia, Sydenham's chorea, Parkinson's disease, Tourette's syndrome, Huntington's disease, amyotrophic lateral sclerosis, multiple sclerosis, muscular dystrophy, Korsakoff's disease, imbecility relating to a cerebral vessel disorder, sleeping disorders, schizophrenia, depression, pain, autism, seasonal affective disorder, jet-lag, depression or other symptoms associated with premenstrual syndrome (PMS), anxiety and septic shock. Compounds of formula (I) may also be expected to show activity in the prevention and reversal of drug addiction or tolerance such as tolerance to opiates and diazepines, treatment of drug addiction, treatment of migraine and other vascular headaches, neurogenic inflammation, in the treatment of gastrointestinal motility disorders and in the induction of labour.

We are particularly interested in the conditions stroke, Alzheimer's disease, Parkinson's disease, multiple sclerosis, schizophrenia, migraine, septic shock and pain.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired.

However, in general, satisfactory results are obtained when the compounds are administered at a dosage of the solid form of between 1 mg and 2000 mg per day.

The compounds of formula (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, inhalation, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt thereof.

According to the invention, we further provide a pharmaceutical composition comprising a compound of formula (I), or a pharmaceutically acceptable salt thereof, in admixture with a pharmaceutically acceptable adjuvant, diluent or carrier.

There is also provided a process for the preparation of such a pharmaceutical composition which comprises mixing the ingredients.

The compounds of formula (I), and pharmaceutically acceptable derivatives thereof, may also be advantageously used in combination with one of the following therapies: NSAIDS, COX-2 inhibitors, Paracetamol, Tramadol, Corticosteroids, Glucosamine, Doxycyclin, Pralnacasan, MMP inhibitors or Coll-3 inhibitors. The compound of formula (I) and the combination therapy may either be formulated together within the same pharmaceutical composition for administration in a single dosage unit, or each component may be individually formulated such that separate dosages may be administered either simultaneously or sequentially.

The invention is illustrated, but in no way limited, by the following examples:

The following abbreviations are used:—DMSO (dimethylsulfoxide), DMF (N,N-dimethylformamide), THF (tetrahydrofuran).

EXAMPLE 1

3-[[(1S)-2-Amino 1-phenylethyl]thio]-5-methyl-2-thiophenecarbonitrile oxalate a) 3-Bromo-5-methyl-2-thiophenecarbonitrile To a suspension of 3-bromo-5-methyl-2-thiophenecarboxaldehyde (500 mg) in water (10 ml) was added hydroxylamine-O-sulfonic acid (330 mg). The mixture was heated to 50° C. for 12 h and allowed to cool. The mixture was then extracted with ethyl acetate (3×50 ml). The combined organic layers were washed (brine), dried (MgSO$_4$), filtered and evaporated to leave the sub-title compound (410 mg) as a brown solid.

$^1$H NMR 300 MHz (CDCl$_3$) 6.79 (1H, s), 2.54 (3H, s).

b) 1,1-Dimethylethyl [(2R)-2-hydroxy-2-phenylethyl]carbamate (R)-α-(Aminomethyl)benzenemethanol (1.70 g) and bis(1,1-dimethylethyl)carbonate (2.98 g) were dissolved in methanol (20 ml) and triethylamine (4.3 ml) added. The mixture was stirred at room temperature for 4 days and then concentrated to leave the sub-title compound as an oil (2.60 g).

$^1$H NMR 300 MHz (CDCl$_3$) 7.27-7.38 (5H, m), 4.92 (1H, m), 4.83 (1H, m), 3.50 (1H, m), 3.25 (1H, m), 1.45 (9H, s)

c) S-[(1S)-2-[[(1,1-Dimethylethoxy)carbonyl]amino]-1-phenylethyl]benzenecarbothioate To a solution of triphenylphosphine (5.75 g) in THF (100 ml) under nitrogen at 0° C. was added diisopropylazodicarboxylate (4.55 ml) dropwise. The mixture was stirred at 0° C. for 45 minutes and then a solution of thiobenzoic acid (3.05 ml) and the product from step (b) (2.60 g) in THF (50 ml) added dropwise at 0° C. After the addition was complete the mixture was stirred at room temperature for 24 h. The mixture was concentrated and the residue purified by chromatography (silica, 10% diethyl ether/isohexane as eluent) to give the sub-title compound (3.30 g) as a yellow solid.

$^1$H NMR 300 MHz (CDCl$_3$) 7.95 (2H, m), 7.56 (1H, m), 7.28-7.44 (7H, m), 4.94 (1H, m), 4.75 (1H, bs), 3.70 (2H, m), 1.38 (9H, s).

d) 1,1-Dimethylethyl [(2S)-2-[(2-cyano-5-methyl-3-thienyl)thio]-2-phenylethyl]carbamate S-[(1S)-2-[[(1,1-Dimethylethoxy)carbonyl]amino]-1-phenylethyl] benzenecarbothioate (210 mg) was dissolved in 7M ammonia in methanol (10 ml) and stirred under nitrogen for 2 h. The solution was evaporated to dryness and the residue dissolved in dry DMF (10 ml). To this solution was added the product from step (a) (120 mg) followed by caesium carbonate (195 mg). The reaction mixture was stirred for 24 h, poured into water and extracted with ethyl acetate (3×50 ml). The combined organic layers were washed with brine and dried (MgSO$_4$). The solvent was evaporated off and the residue purified by chromatography (silica, 20% ethyl acetate/isohexane as eluent) to give the sub-title compound as an oil (65 mg).

MS (APCI+ve)$^m$/z 275 [M+H-BOC]$^+$.

e) 3-[[(1S)-2-Amino-1-phenylethyl]thio]-5-methyl-2-thiophenecarbonitrile oxalate To a solution of the product from step (d) (65 mg) in methanol (5 ml) was added 4M HCl in dioxane (5 ml). The mixture was stirred at 20° C. for 2 h and the solvent was removed in vacuo. The residue was partitioned between aqueous sodium bicarbonate and ethyl acetate. The aqueous phase was extracted with ethyl acetate (2×50 ml) and the combined extracts were washed with brine, dried (MgSO$_4$), filtered and concentrated in vacuo. The residue was dissolved in ethyl acetate and a solution of oxalic acid in diethyl ether added. The solution was filtered and dried to give the title compound as a white solid (11 mg).

MS (APCI+ve)$^m$/z 275 [M(+H)]$^+$. $^1$H NMR 400 MHz (DMSO-d$_6$) 7.38 (5H, m), 7.19 (1H, s), 4.74 (1H, m), 3.48 (1H, m), 3.28 (1H, m), 2.50 (3H, s).

Screens

The pharmacological activity of compounds according to the invention was tested in the following screens.

Screen 1

The activity of compounds of formula (I), or a pharmaceutically acceptable salt, enantiomer or racemate thereof, may be screened for nitric oxide synthase inhibiting activity by a procedure based on that of Förstermann et al., Eur. J. Pharm., 1992, 225, 161-165. Nitric oxide synthase converts $^3$H-L-arginine into $^3$H-L-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbeccos Modified Eagles Medium (DMEM) supplemented with 10% foetal bovine serum, 4 mM L-glutamine and antibiotics (100 units/ml penicillin G, 100 mg/ml streptomycin & 0.25 mg/ml amphotericin B). Cells are routinely grown in 225 cm$^3$ flasks containing 35 ml medium kept at 37° C. and in a humidified atmosphere containing 5% CO$_2$.

Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17-20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 1 mM dithiothreitol and a cocktail of protease inhibitors comprising leupeptin (2 mg/ml), soya bean trypsin inhibitor (10 mg/ml), aprotinin (5 mg/ml) and phenylmethylsulphonyl fluoride (50 mg/ml).

For the assay, 25 µl of substrate cocktail (50 mM Tris-HCl (pH 7.5 at 20° C.), 400 µM NADPH, 20 µM flavin adenine dinucleotide, 20 µM flavin mononucleotide, 4 µM tetrahydrobiopterin, 12 µM L-arginine and 0.025 mCi L-[$^3$H] arginine) is added to wells of a 96 well filter plate (0.45 µM pore size) containing 25 µl of a solution of test compound in 50 mM Tris-HCl. The reaction is started by adding 50 µl of cell lysate (prepared as above) and after incubation for 1 hour at room temperature is terminated by addition of 50 µl of an aqueous solution of 3 mM nitroarginine and 21 mM EDTA.

Labelled L-citrulline is separated from labelled L-arginine using Dowex AG-50W. 150 µl of a 25% aqueous slurry of Dowex 50W (Na$^+$ form) is added to the assay after which the whole is filtered into 96 well plates. 75 µl of filtrate is sampled and added to wells of 96 well plates containing solid scintillant. After allowing the samples to dry the L-citrulline is quantified by scintillation counting.

In a typical experiment basal activity is 300 dpm per 75 µl sample which is increased to 1900 dpm in the reagent controls. Compound activity is expressed as IC$_{50}$ (the concentration of drug substance which gives 50% enzyme inhibition in the assay) and aminoguanidine, which gives an IC$_{50}$ (50% inhibitory concentration) of 10 µM, is tested as a standard to verify the procedure. Compounds are tested at a range of concentrations and from the inhibitions obtained IC$_{50}$ values are calculated. Compounds that inhibit the enzyme by at least 25% at 100 µM are classed as being active and are subjected to at least one retest.

In the above screen, the compound of Example 1 was tested and gave an IC$_{50}$ value of less than 10 µM indicating that it is expected to show useful therapeutic activity.

Screen 2

Recombinant human NO synthases (iNOS, eNOS & nNOS) were expressed in E. coli and lysates were prepared in Herpes buffer (pH 7.4) containing co-factors (FAD, FMN, H$_4$B), protease inhibitors, lysozyme and the detergent, CHAPS. These preparations were used, at suitable dilution, to assess inhibition of the various isoforms. Inhibition of NOS was determined by measuring the formation of L-[$^3$H] citrulline from L-[$^3$H]arginine using an adaptation of the method of Förstermann et al.[9] Enzyme assays were performed in the presence of 3 µM [$^3$H]arginine, 1 mM NADPH and other co-factors required to support NOS activity (FAD, FMN, H$_4$B, calmodulin, Ca$^{2+}$). Since various NOS inhibitors have been reported to exhibit slow binding kinetics, or to inactivate the enzyme in a time dependent manner, enzyme and inhibitor were pre-incubated for 60 min in the presence of NADPH before addition of arginine to initiate the reaction. Incubations continued for a further 60 min before the assays were quenched and [$^3$H]citrulline separated from unreacted substrate by chromatography on Dowex-50W resin in a 96-well format.

In the above screen, the compound of Example 1 was tested and gave an IC$_{50}$ value of less than 10 µM against the INOS enzyme indicating that it is expected to show useful therapeutic activity.

Screen 3

Compounds also show activity against the human form of induced nitric oxide synthase as can be demonstrated in the following assay.

The human colorectal carcinoma cell line, DLD-1 (obtained from the European Collection of Animal Cell Culture—cell line number 90102540) was routinely grown in RPMI 1640 supplemented with 10% (v/v) foetal bovine serum, and 2 mM L-glutamine, at 37° C. in 5% CO$_2$.

Nitric oxide synthase was induced in cells by addition of medium containing human recombinant gamma-IFN (1000 units/ml), TNF-alpha (200 U/ml), IL-6 (200 U/ml) and IL-1-beta (250 U/ml). After incubation for 18 hours at 37° C., the medium was removed and the cells washed with warm phosphate buffered saline. Cells were incubated for a further 5 hours at 37° C./5% $CO_2$ in RPMI 1640 containing 100 µM L-arginine and 100 µM verapamil-HCl in the presence and absence of test compounds.

Nitrite accumulation was determined by mixing an equal volume of culture media with Griess reagent (10 mg/ml sulphanilamide, 1 mg N-(1-naphthyl)ethylenediamine in 1 ml 2.5% (v/v) phosphoric acid). Inhibition in the presence of compounds was calculated relative to the nitrite levels produced by untreated cells. $IC_{50}$ values were estimated from a semi-log plot of % inhibition versus concentration of compound.

In the above screen, the compound of Example 1 was tested and gave an $IC_{50}$ value of less than 100 µM indicating that it is expected to show useful therapeutic activity.

The invention claimed is:

1. A compound of formula (I)

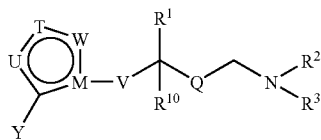

(I)

wherein:
- Y represents C1 to 4 alkoxy, halogen, CN, C≡CH, $NO_2$, $CH_2OH$, CHO, $COCH_3$, $NH_2$, NHCHO, $NHCOCH_3$, or $NHSO_2CH_3$; said alkoxy group being optionally further substituted by one or more fluorine atoms;
- T, U and W independently represent CX or $S(O)_m$, except that at least one of T, U and W must represent a heteroatom and except that not more than one of T, U and W may represent $S(O)_m$; m represents an integer 0, 1 or 2; and each X group independently represents H, C1 to 4 alkyl, C1 to 4 alkoxy, halogen, OH, SH, CN, C≡CH, $N(R^{11})_2$, $NO_2$, $CH_2OH$, CHO, $COCH_3$ or NHCHO; said alkyl or alkoxy group being optionally further substituted by one or more fluorine atoms;
- V represents $NR^4$, O, $CH_2$, $S(O)_n$, $OCH_2$, $CH_2O$, $NR^4CH_2$, $CH_2NR^4$, $CH_2S(O)_n$, $S(O)_nCH_2$, $CH_2CH_2$ or CH=CH;
- n represents an integer 0, 1 or 2;
- M represents C;
- $R^{10}$ represents H or Me;
- Q represents $(CH_2)_p$ and p represents an integer 0, 1, 2 or 3;
- $R^1$ represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^5R^6$; said alkyl or alkoxy group being optionally further substituted by one or more fluorine atoms;
- $R^2$ and $R^3$ independently represent H, C1 to 4 alkyl or C3 to 6 cycloalkyl; said alkyl group being optionally substituted by C1 to 4 alkoxy, halogen, hydroxy, -Z-$NR^7R^8$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$;
- Z represents —CO— or a bond;
- $R^4$ and $R^{11}$ independently represent H or C1 to 2 alkyl;
- $R^5$, $R^6$, $R^7$ and $R^8$ independently represent H or C1 to 4 alkyl; and
- $R^9$ represents H, C1 to 4 alkyl, CHO, $COCH_3$, $SO_2CH_3$ or $CF_3$;

or a pharmaceutically acceptable salt thereof.

2. A compound according to claim 1 wherein Y represents CN.

3. A compound of formula (I), according to claim 1, which is:
3-[[(1S)-2-amino-1-phenylethyl]thio]-5-methyl-2-thiophenecarbonitrile;
or a pharmaceutically acceptable salt, enantiomer or racemate thereof.

4. A pharmaceutical composition comprising a compound of formula (I) according to claim 1, or a pharmaceutically acceptable salt thereof, in admixture with a pharmaceutically acceptable adjuvant, diluent or carrier.

5. A method, of treating pain, comprising administering to a subject in need thereof a compound of formula (I)

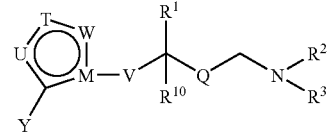

(I)

wherein:
- Y represents C1 to 4 alkyl, C1 to 4 alkoxy, halogen, CN, C≡CH, $NO_2$, $CH_2OH$, CHO, $COCH_3$, $NH_2$, NHCHO, $NHCOCH_3$, or $NHSO_2CH_3$; said alkyl or alkoxy group being optionally further substituted by one or more fluorine atoms;
- T, U and W independently represent CX or $S(O)_m$, except that at least one of T, U and W must represent a heteroatom and except that not more than one of T, U and W may represent $S(O)_m$; m represents an integer 0, 1 or 2; and each X group independently represents H, C1 to 4 alkyl, C1 to 4 alkoxy, halogen, OH, SH, CN, C≡H, $N(R^{11})_2$, $NO_2$, $CH_2OH$, CHO, $COCH_3$ or NHCHO; said alkyl or alkoxy group being optionally further substituted by one or more fluorine atoms;
- V represents $NR^4$, O, $CH_2$, $S(O)_n$, $OCH_2$, $CH_2O$, $NR^4CH_2$, $CH_2NR^4$, $CH_2S(O)_n$, $S(O)_nCH_2$, $CH_2CH_2$ or CH=CH;
- n represents an integer 0, or 2;
- M represents C;
- $R^{10}$ represents H or Me;
- Q represents $(CH_2)_p$ and p represents an integer 0, 1, 2 or 3;
- $R^1$ represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, NO$_2$ or NR$^5$R$^6$; said alkyl or alkoxy group being optionally further substituted by one or more fluorine atoms;

R$^2$ and R$^3$ independently represent H, C1 to 4 alkyl or C3 to 6 cycloalkyl; said alkyl group being optionally substituted by C1 to 4 alkoxy, halogen, hydroxy, -Z-NR$^7$R$^8$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, CF$_3$, OCF$_3$, CN or NO$_2$;

Z represents —CO— or a bond;

R$^4$ and R$^{11}$ independently represent H or C1 to 2 alkyl;

R$^5$, R$^6$, R$^7$ and R$^8$ independently represent H or C1 to 4 alkyl; and

R$^9$ represents H, C1 to 4 alkyl, CHO, COCH$_3$, SO$_2$CH$_3$ or CF$_3$;

or a pharmaceutically acceptable salt thereof.

6. A process for the preparation of a compound of formula (I),

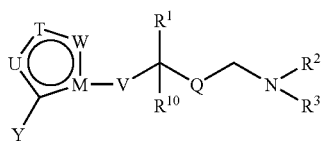

(I)

wherein:

Y represents C1 to 4alkyl, C1 to 4alkoxy, halogen, CN, C≡CH, NO$_2$, CH$_2$OH, CHO, COCH$_3$, NH$_2$, NHCHO, NHCOCH$_3$, or NHSO$_2$CH$_3$; said alkyl or alkoxy group being optionally further substituted by one or more fluorine atoms;

T, U and W independently represent CX or S(O)$_m$, except that at least one of T, U and W must represent a heteroatom and except that not more than one of T, U and W may represent S(O)$_m$; m represents an integer 0, 1 or 2; and each X group independently represents H, C1 to 4 alkyl, C1 to 4 alkoxy, halogen, OH, SH, CN, C≡H, N(R$^{11}$)$_2$, NO$_2$, CH$_2$OH, CHO, COCH$_3$ or NHCHO; said alkyl or alkoxy group being optionally further substituted by one or more fluorine atoms;

V represents NR$^4$, O, CH$_2$, S(O)$_n$, OCH$_2$, CH$_2$O, NR$^4$CH$_2$, CH$_2$NR$^4$, CH$_2$S(O)$_n$, S(O)$_n$CH$_2$, CH$_2$CH$_2$ or CH=CH;

n represents an integer 0, 1 or 2;

M represents C;

R$^{10}$ represents H or Me;

Q represents (CH$_2$)$_p$ and p represents an integer 0, 1, 2 or 3;

R$^1$ represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, NO$_2$ or NR$^5$R$^6$; said alkyl or alkoxy group being optionally further substituted by one or more fluorine atoms;

R$^2$ and R$^3$ independently represent H, C1 to 4 alkyl or C3 to 6 cycloalkyl; said alkyl group being optionally substituted by C1 to 4 alkoxy, halogen, hydroxy, -Z-NR$^7$R$^8$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, CF$_3$, OCF$_3$, CN or NO$_2$;

Z represents —CO— or a bond;

R$^4$ and R$^{11}$ independently represent H or C1 to 2 alkyl;

R$^5$, R$^6$, R$^7$ and R$^8$ independently represent H or C1 to 4 alkyl;

R$^9$ represents H, C1 to 4 alkyl, CHO, COCH$_3$, SO$_2$CH$_3$ or CF$_3$;

or a pharmaceutically acceptable salt, enantiomer or racemate thereof, wherein the process comprises:

(a) reaction of a compound of formula (II)

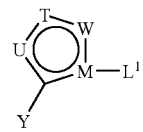

(II)

wherein L$^1$ represents a leaving group, with a compound of formula (III)

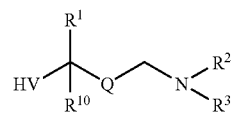

(III)

or (b) reaction of a compound of formula (IV)

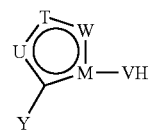

(IV)

with a compound of formula (V)

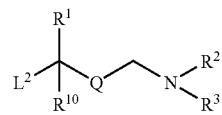

(V)

wherein L$^2$ is a leaving group; or (c) reaction of a compound of formula (VI)

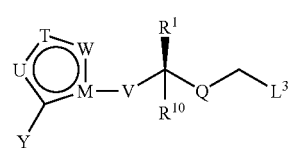

(VI)

wherein L$^3$ is a leaving group, with a compound of formula (VII)

R²R³NH    (VII)

or (d) reduction of a compound of formula (VIII)

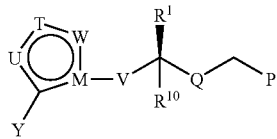
(VIII)

wherein P represents azide (N₃); or (e) hydrolysis of a compound of formula (VIII)

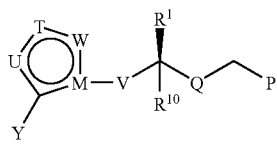
(VIII)

wherein P represents an imide group;

and where desired or necessary converting the resultant compound of formula (I), or another salt thereof, into a pharmaceutically acceptable salt thereof; or converting one compound of formula (I) into another compound of formula (I); and where desired converting the resultant compound of formula (I) into an optical isomer thereof.

7. A compound of formula (I)

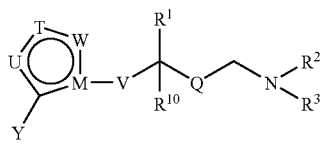
(I)

wherein:

Y represents C1 to 4 alkyl, C1 to 4 alkoxy, halogen, CN, C≡CH, NO₂, CH₂OH, CHO, COCH₃, NH₂, NHCHO, NHCOCH₃, or NHSO₂CH₃; said alkyl or alkoxy group being optionally further substituted by one or more fluorine atoms;

T, U and W independently represent CX or S(O)$_m$, except that at least one of T, U and W must represent a heteroatom and except that not more than one of T, U and W may represent S(O)$_m$; m represents an integer 0, 1 or 2; and each X group independently represents H, C1 to 4 alkyl, C1 to 4 alkoxy, halogen, OH, SH, CN, C≡CH, N(R¹¹)₂, NO₂, CH₂OH, CHO, COCH₃ or NHCHO; said alkyl or alkoxy group being optionally further substituted by one or more fluorine atoms;

V represents S(O)$_n$;

n represents an integer 0;

M represents C;

R¹⁰ represents H or Me;

Q represents (CH₂)$_p$ and p represents an integer 0, 1, 2 or 3;

R¹ represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, NO₂ or NR⁵R⁶; said alkyl or alkoxy group being optionally further substituted by one or more fluorine atoms;

R² and R³ independently represent H, C1 to 4 alkyl or C3 to 6 cycloalkyl; said alkyl group being optionally substituted by C1 to 4 alkoxy, halogen, hydroxy, -Z-NR⁷R⁸, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, CF₃, OCF₃, CN or NO₂;

Z represents —CO— or a bond;

R⁴ and R¹¹ independently represent H or C1 to 2 alkyl;

R⁵, R⁶, R⁷ and R⁸ independently represent H or C1 to 4 alkyl; and

R⁹ represents H, C1 to 4 alkyl, CHO, COCH₃, SO₂CH₃ or CF₃;

or a pharmaceutically acceptable salt thereof.

* * * * *